United States Patent [19] [11] 4,390,742
Wideman [45] Jun. 28, 1983

[54] REDUCTION OF CYCLOPENTADIENE FROM ISOPRENE STREAMS

[75] Inventor: Lawson G. Wideman, Tallmadge, Ohio

[73] Assignee: The Goodyear Tire & Rubber Company, Akron, Ohio

[21] Appl. No.: 350,915

[22] Filed: Feb. 22, 1982

[51] Int. Cl.³ .......................... C07C 7/01; C07C 7/12
[52] U.S. Cl. .................................. 585/854; 585/810; 585/820; 585/829
[58] Field of Search ............... 585/809, 810, 820, 829, 585/853, 854

[56] References Cited
U.S. PATENT DOCUMENTS
4,232,182  11/1980  Liakumonich et al. ............ 585/854

Primary Examiner—Delbert E. Gantz
Assistant Examiner—A. Pal
Attorney, Agent, or Firm—Bruce J. Hendricks

[57] ABSTRACT

A process for reducing the level of cyclopentadiene present in a hydrocarbon stream containing isoprene and cyclopentadiene which involves contacting the stream with an alkali metal hydroxide wherein the reaction product is an insoluble salt of CPD.

8 Claims, No Drawings

REDUCTION OF CYCLOPENTADIENE FROM ISOPRENE STREAMS

BACKGROUND OF THE INVENTION

This application is directed to the reduction of very minute quantities of cyclopentadiene (hereinafter referred to as CPD) from hydrocarbon streams. It has been found that a number of hydrocarbon streams, particularly those containing mixtures of C-5 saturated hydrocarbons and unsaturated hydrocarbons containing, for instance, isoprene, pentane, pentene and CPD are of commercial value. However, CPD or dicyclopentadiene have an inhibiting effect on the subsequent polymerization of isoprene to cis-1, 4-polyisoprene. In the polymerization reaction, the Ziegler-Natta catalyst tends to be poisoned by the CPD.

To a large extent, many of the undesirable compounds can be removed by means of distillation of the hydrocarbon stream. However, because the boiling points of the C-5 hydrocarbon are very close, it is necessary to carry out distillation in columns having a large number of trays in order to achieve an adequate degree of separation. Such a distillation has been found to be technically and economically unattractive.

One known method for removal of CPD consists in binding CPD by carbonyl compounds such as benzaldehyde, salicylaldehyde, acetophenone, cyclopentanone in the presence of alkali metal alcoholates with the formation of the respective fulvenes. A decontaminated hydrocarbon is further treated with sodium bisulfite and water to remove said carbonyl compound and the fulvenes are distilled off. The disadvantage of this method is that the alkali metal alcoholate used therein as a catalyst is expensive and requires thorough dessication of the decontaminated hydrocarbon, the consumption of the catalyst being important since it is decomposed by water released during the binding of cyclopentadiene. Furthermore, the carbonyl compounds used are capable of being polymerized under the conditions of hydrocarbons decontamination resulting in clogging of equipment and excluding the possibility of stable operational conditions.

It is also possible to remove CPD from hydrocarbon mixtures by thermal dimerization and separation of the dimerized product from other hydrocarbons, such as isoprene, by means of distillation. However, dimerization takes a long time to decrease the amount of CPD to the very low concentrations permissible for isoprene polymerization, and still requires separation by distillation. Moreover, the resultant CPD dimers are of little commercial value.

Another known method for the removal of 1,3-CPD from an isoprene stream is by the addition of a solution of maleic anhydride in dimethyl formamide. The solution has a weight ratio of maleic anhydride to dimethyl formamide of about 2:1. This solution is added to the isoprene stream to give a 1.6 percent solution by weight which is allowed to react for 1½ hours without agitation. The CPD-maleic anhydride adduct and unreacted maleic anhydride are then removed from the isoprene stream by use of a caustic scrubber such as aqueous sodium hydroxide.

One known method for the removal of CPD from a hydrocarbon mixture containing isoprene consists of contacting the isoprene mixture with dehydrated molecular sieve material containing at least one alkali metal and having a pore diameter of more than 0.6 nanometers.

Another known method of decontaminating hydrocarbons used as solvents and monomers in the production of synthetic rubber by stereospecific polymerization from CPD which is present in the amount of 0.001–0.5 percent by weight of said hydrocarbons, comprises treating a mixture of said hydrocarbons and CPD with acyclic ketone having from 6 to 12 carbon atoms at a 10–2000 times stoichiometric-excess of said ketone with respect to CPD in the presence of a catalyst selected from the group consisting of alkali metal hydroxide or an anionic exchange resin in the (OH—) form thus obtaining a fulvene, said treatment taking place in the presence of 50 to 60 percent of a fulvene by weight of the hydrocarbons being decontaminated, said fulvene having been recycled together with unreacted ketone from a previous distillation of decontaminated hydrocarbons; and distilling off the decontaminated hydrocarbons containing not more than 0.0001 percent by weight of CPD. The disadvantage of this method is the required distillation of the hydrocarbon mixture.

Still another known process for purifying isoprene from mixtures thereof with carbonyl compounds and CPD produced by the catalytic decomposition of dimethyldioxane consists of the steps of passing the isoprene mixture at a temperature of from 40° to 70° C. through a bed of solid product which comprises an anion exchange resin or alkali, and subjecting said isoprene mixture to fractionation with at least 50 theoretical plates and a reflux ratio of at least 3, recycling 20 to 80 weight percent of said purified isoprene following close fractionation for admixture with the starting isoprene to be purified.

SUMMARY OF THE INVENTION

Disclosed is a process for the removal of small amounts of CPD from a C-5 hydrocarbon stream which comprises contacting said stream with an alkali metal hydroxide representative of the group potassium hydroxide and sodium hydroxide.

DETAILED DESCRIPTION OF PREFERRED EMBODIMENTS

According to the present invention, there is provided a process for reducing amounts of CPD present in a hydrocarbon stream, particularly those containing mixtures of C-5 saturated hydrocarbons and unsaturated hydrocarbons containing, for instance, isoprene, pentane and pentene, comprising passing said stream through a bed of material which comprises an alkali metal hydroxide.

One advantage of the present invention is that this process reduces the presence of CPD in a hydrocarbon stream to a tolerable level in the absence of subsequent distillation of the said stream. This advantage will result in substantial savings in economy and time.

In practicing the present invention, the C-5 stream may be contacted with the catalyst wherein the C-5 stream is in a vapor or liquid phase. The temperature may be selected within a wide range, preferably selected between 0° C. and 100° C. At temperatures above 100° C. there is a risk of polymerization of isoprene, whereas cooling of the hydrocarbon mixture to temperatures below 0° C. is often difficult. It is believed that when the CPD present in the C-5 stream comes in contact with the alkali metal hydroxide bed, the respective insoluble salt is formed in the bed. The fact remains that when the CPD in the hydrocarbon stream is collected in the bed, it eliminates the requirements of subsequent distillation of the C-5 stream.

Liquid hour space velocity, hereinafter known as LHSV, is meant to mean a volume of liquid throughout per gross volume of catalyst which is the actual volume plus the interstitial volume. For example, 90 ml of liquid feed stock is passed over 45 cc (gross volume) of catalyst in one hour to yield a LHSV value of 2. See *Chemical Engineering Kinetics*, J. M. Smith, MacGraw-Hill, New York, pages 99–100 (1956). The LHSV of the volume of the feed stream is measured as the stream approaches the bed of catalyst. As one skilled in the art would realize, if one has an excessive LHSV, the residence time of the feed stream with the catalyst will be insufficient to convert the CPD to an insoluble salt.

Accordingly, if the LHSV is too low, it results in a residence time which would be commercially unfeasible. Preferably, the LHSV value is from 0.1 to 30; more preferably, from 0.48 to 10.

The alkali metal hydroxide may be used in any form which permits good contact with the C-5 hydrocarbon stream to be treated, for example, in the form of powders, pills, granules, cylinders, tablets, etc. Preferably, the diameter of the form is such that it can pass through an 80 mesh screen. Mesh is to designate the number of openings per linear inch of screen, i.e., 80 mesh meaning 80 openings per linear square inch.

The alkali metal hydroxide can be employed without an inert carrier; however, it is advisable to use the alkali metal hydroxide on an inert carrier to further increase the surface area of the catalyst. Examples of such inert carriers can be selected from the group comprising silica gel, corundum, celite, $Al_2O_3$ and $SiO_2$.

Supporting the alkali metal hydroxide can be any support that does not detrimentally effect the activity of the alkali metal hydroxide and has a good surface area of at least 10 $m^2/gm$.

The alkali metal hydroxide may contain from about 1 to 50 percent of the weight of the loaded alkali metal hydroxide. Accordingly, the support comprises from 99 to 50 percent by weight based on the loaded alkali metal hydroxide. Preferably, the loaded alkali metal hydroxide comprises 10 to 40 percent by weight of the alkali metal hydroxide.

The following examples are supplied in order to illustrate, but not necessarily to limit, the process of the present invention. All percentages are based on percentages by weight of overall stream unless specifically stated otherwise.

EXAMPLE 1-17

50 ml of a C-5 hydrocarbon stream containing 5.2% isoprene and 12.2 ppm of CPD (based on the stream) was contacted with varying amounts of alkali metal hydroxides. All samples were mechanically agitated during the residence time to insure efficient contact of the stream with the alkali metal hydroxides. The agitation was on a Burrell shaker. After agitation the alkali metal hydroxide—C-5 hydrocarbon stream was filtered and analyzed. As reflected in Table I, various forms (i.e., powdered and pellets) of the alkali hydroxides were tested. As reflected in Table I, varying residence times were conducted.

TABLE I

| Ex. | Catalyst Form & | Amount | Residence Time (hr) | Isoprene Removal (%) | CPD Reduction (%) |
|---|---|---|---|---|---|
| 1 | NaOH Pellets (¼" diameter) | (1.0g) | 16 | 0 | 34 |
| 2 | NaOH Powder (less than 80 mesh) | (1.0g) | 16 | 0 | 34 |
| 3 | NaOH Powder (less than 80 mesh) | (5.0g) | 16 | 0 | 92 |
| 4 | NaOH Powder (less than 80 mesh) | (10.0g) | 16 | 0 | 100 |
| 5 | KOH Powder (less than 80 mesh) | (5.0g) | 16 | 0 | 100 |
| 6 | KOH Powder (less than 80 mesh) | (10.0g) | 16 | 0 | 100 |
| 7 | KOH Powder (less than 80 mesh) | (20.0g) | 1 | 0 | 100 |
| 8 | NaOH Powder (less than 80 mesh) | (20.0g) | 4 | 0 | 100 |
| 9 | KOH Powder (less than 80 mesh) | (20.0g) | 16 | 0 | 100 |
| 10 | KOH Powder (less than 80 mesh) | (5.0g) | ½ | 0 | 100 |
| 11 | KOH Powder (less than 80 mesh) | (5.0g) | 16 | 0 | 100 |
| 12 | KOH Powder (less than 80 mesh) | (10.0g) | 16 | 0 | 100 |
| 13 | KOH Powder (less than 80 mesh) | (20.0g) | 1 | 0 | 100 |
| 14 | KOH Powder (less than 80 mesh) | (1.0g) | ½ | 0 | 9 |
| 15 | KOH Powder (less than 80 mesh) | (1.0g) | 1 | 0 | 54 |
| 16 | KOH Powder (less than 80 mesh) | (1.0g) | 2 | 0 | 65 |
| 17 | KOH Powder (less than 80 mesh) | (1.0g) | 4 | 0 | 100 |

EXAMPLE 18

200 ml of a high purity isoprene stream (98–99%) containing 18 ppm of CPD (based on the isoprene content) was contacted with 20 grams of KOH powder. The residence time of the stream was 20 minutes. The KOH powder-isoprene stream was filtered and then subjected to analysis. The analysis showed the stream contained 98–99% isoprene with 0 ppm of CPD.

EXAMPLE 19-20

A fixed-bed continuous reaction was carried out by directly adding 75 cc of powdered KOH into the reactor. A C-5 hydrocarbon stream containing 5.2% by weight of isoprene in 12 ppm of CPD (based on overall weight of stream) was contacted with the bed of powdered KOH. The hydrocarbon stream was metered at 23° C. in a down-flow manner over the powdered KOH. The stream had an LHSV value of 0.48. The reactor was at atmospheric pressure and the C-5 effluent was received in a dry ice/acetone-cooled vessel. A nitrogen carrier gas with the flow of 7 ml/min was used in a co-current direction. Table II lists the results.

TABLE II

| Ex. | Catalyst Form | Residence Time (hr) | Removal Isoprene (%) | Removal CPD (%) |
|---|---|---|---|---|
| 19 | Powdered KOH (less than 80 mesh) | 1 | 0 | 100 |
| 20 | Powdered KOH (less than 80 mesh) | 2 | 0 | 100 |

For the purpose of comparison, various types of compounds were contacted with a C-5 hydrocarbon stream containing 5.2% by weight of isoprene and 12 ppm of CPD (based on overall weight of stream). All of the following non-alkali metal hydroxide reactions were carried out in a heat dried 100 ml vessel under nitrogen.

TABLE III

| Ex. | Bed Constituents | Amount | C$_5$ Stream (ml) | Removed Isoprene (%) | CPD (%) |
|---|---|---|---|---|---|
| 21 | BH$_3$/THF | (0.98 mmol) | 20 | 23 | 35 |
| 22 | CuCl | (1.0 mmol) | 20 | 2 | 18 |
| 23 | FeCl$_3$ | (1.0 mmol) | 20 | 81 | 100 |
| 24 | AlCl$_3$ | (1.0 mmol) | 20 | 11 | 65 |
| 25 | 3A Molecular Sieves | (1 g) | 20 | 8 | 59 |
| 26 | 4A Molecular Sieves | (1 g) | 20 | 6 | 29 |
| 27 | 10 × (8A) Molecular Sieves | (1 g) | 20 | 25 | 53 |
| 28 | Amberlyst (ion exchange Resin) XN-1010 | (0.5 g) | 50 | 9 | 47 |
| 29 | T-1 Raney Nickel | (1 g) | 50 | 13 | 59 |
| 30 | Active (Dehydrated) Al$_2$O$_3$ | (0.5 g) | 50 | 2 | 54 |
| 31 | Co octoate (Reduced) w/triethyl aluminum | (0.25 mmol) | 20 | 11 | 35 |
| 32 | Fe octoate (Reduced) w/triethyl aluminum | (0.25 mmol) | 20 | 13 | 24 |

EXAMPLE 33–36

50 ml of a C-5 hydrocarbon stream containing 57% isoprene, 24 ppm of CPD, 38 ppm of 1-pentyne, 44 ppm of isopryne and 59 ppm of 2-pentyne, was contacted with various amounts of powdered KOH (diameter of less than 80 mesh) Table IV lists the reduction results of CPD in the presence of other C-5 hydrocarbons. The residence time was 4 hours.

TABLE IV

| Ex. | Isoprene % | CPD (ppm) | 1-Pentyne (ppm) | Isopryne (ppm) | 2-Pentyne (ppm) |
|---|---|---|---|---|---|
| Control | 57 | 24 | 38 | 44 | 59 |
| After Treatment with Powdered KOH <80 mesh: | | | | | |
| KOH | | | | | |
| 33 .1g | 57 | 19 | 38 | 45 | 60 |
| 34 .5g | 57 | 17 | 40 | 47 | 59 |
| 35 1.0g | 57 | 0 | 38 | 46 | 60 |
| 36 5.0g | 57 | 0 | 35 | 44 | 59 |

EXAMPLE 37–40

50 ml of a C-5 hydrocarbon stream containing 58% isoprene and 8 ppm of CPD, 13 ppm of 1-Pentyne, 17 ppm of Isopryne and 19 ppm of 2-Pentyne was contacted with various amounts of powdered KOH (diameter of less than 80 mesh). Table V lists the reduction results of CPD in the presence of other C-5 hydrocarbons. The residence time was 4 hours.

TABLE V

| Ex. | % Isoprene | CPD (ppm) | 1-Pentyne (ppm) | Isopryne (ppm) | 2-Pentyne (ppm) |
|---|---|---|---|---|---|
| Control | 58 | 8 | 13 | 17 | 19 |
| After Treatment with Powdered KOH <80 mesh: | | | | | |
| KOH | | | | | |
| 37 .5g | 58 | 6 | 13 | 16 | 22 |
| 38 1.0g | 58 | 3 | 14 | 16 | 23 |
| 39 2.0g | 58 | 0 | 11 | 15 | 24 |
| 40 3.0g | 58 | 0 | 11 | 14 | 23 |

EXAMPLE 41–44

Fixed bed continuous reactions were carried out by directly adding 75 cc of powdered KOH into the reactor. A C-5 hydrocarbon stream containing 5% by weight of isoprene, 95% N-pentane and 14 ppm of CPD (based on overall weight of stream) was contacted with the bed of KOH. The hydrocarbon stream was metered at 23° C. in an up-flow manner through the reactor. The stream flow rates and KOH particle size were varied. Analysis of the product streams are given in ppm of CPD. See Table VI.

TABLE VI

| | | Particle Size Ranges (Inches) | | |
|---|---|---|---|---|
| Ex. | LHSV | .0017 | .0117–.0234 | .0234–.0787 |
| 41 | 3.98 | 0 | 0 | .9 ppm |
| 42 | 7.96 | 0 | 1.1 ppm | 3.0 ppm |
| 43 | 15.92 | 1.0 ppm | 5.8 ppm | 11.3 ppm |
| 44 | 23.89 | 1.5 ppm | 11.4 ppm | 12.5 ppm |

While certain representative embodiments and details have been shown for the purpose of illustrating the invention, it will be apparent to those skilled in this art that various changes and modifications may be made therein without departing from the scope of the invention.

I claim:

1. A process for reducing the level of cyclopentadiene present in a C-5 hydrocarbon stream containing no carbonyl compounds comprising forming the respective insoluble salt by contacting said stream with an alkali metal hydroxide, said alkali metal hydroxide being selected from the group consisting of sodium hydroxide, potassium hydroxide, and lithium hydroxide.

2. A process according to claim 1 wherein the alkali metal hydroxide is mounted on an inert carrier.

3. A process according to claim 2 wherein said inert carrier is selected from the group comprising oxide of silicon, corundum, celite and aluminum oxide.

4. A process according to claim 1 wherein said stream has an LHSV value of 0.1 to 30.

5. A process according to claim 1 wherein said alkali metal hydroxide is powdered potassium hydroxide.

6. A process according to claim 4 wherein said stream has an LHSV value of 0.48.

7. A process according to claim 1 wherein said stream is at a temperature from 0° C. to 100° C.

8. A process for reducing the level of CPD present in a C-5 hydrocarbon stream containing isoprene and CPD comprising contacting said stream with an alkali metal hydroxide wherein said reaction product of CPD and the alkali metal hydroxide is an insoluble salt compound.

* * * * *